US007538077B2

(12) United States Patent
Sichmann et al.

(10) Patent No.: US 7,538,077 B2
(45) Date of Patent: May 26, 2009

(54) EXTRUDED PERSONAL WASHING BARS WITH PLATE-LIKE POLYMERIC INCLUSIONS

(75) Inventors: Maiangela Gomes de Oliveira Sichmann, Sao Paulo (BR); Anelise Pineli, Sao Paulo (BR)

(73) Assignee: Conopco, Inc., Englewood Cliffs, NJ (US)

( * ) Notice: Subject to any disclaimer, the term of this patent is extended or adjusted under 35 U.S.C. 154(b) by 220 days.

(21) Appl. No.: 11/768,555

(22) Filed: Jun. 26, 2007

(65) Prior Publication Data

US 2009/0005290 A1 Jan. 1, 2009

(51) Int. Cl.
*A61K 7/50* (2006.01)

(52) U.S. Cl. ....................... 510/141; 510/147; 510/152; 510/475

(58) Field of Classification Search ....................... None
See application file for complete search history.

(56) References Cited

U.S. PATENT DOCUMENTS

| | | | | |
|---|---|---|---|---|
| 3,723,325 | A | 3/1973 | Parran, Jr. | |
| 3,864,272 | A | 2/1975 | Toma et al. | |
| 4,720,365 | A | 1/1988 | Schonig et al. | |
| 6,664,217 | B1 | 12/2003 | Puvvada et al. | |
| 6,730,642 | B1 | 5/2004 | Aronson et al. | |
| 2003/0108501 | A1 * | 6/2003 | Hofrichter et al. | 424/70.1 |
| 2003/0219464 | A1 | 11/2003 | Incando et al. | |
| 2005/0084470 | A1 | 4/2005 | Abbas | |
| 2005/0123574 | A1 | 6/2005 | Abbas et al. | |

FOREIGN PATENT DOCUMENTS

| | | | |
|---|---|---|---|
| WO | 2006/009625 | A1 | 1/2006 |

* cited by examiner

*Primary Examiner*—Necholus Ogden, Jr.
(74) *Attorney, Agent, or Firm*—Michael P. Aronson

(57) ABSTRACT

An extruded personal washing bar providing unique combination of sensory attributes, said bar comprising:

a. at least about 40% of a soap,
b. from about 0.1% to about 20% of a polyol,
c. no more than about 30% water, and
d. from about 0.01% to about 3% based on the weight of the bar composition of inclusions dispersed uniformly in bar, said inclusions comprising plate-like solid polymer particles, having a longest edge dimension in the range from about 50 to about 300 μm, and a thickness such that the ratio of the longest edge dimension to the thickness is in the range from about 1.5:1 to about 15:1, and wherein said personal washing bar is an extruded mass.

19 Claims, 1 Drawing Sheet

EXTRUDED PERSONAL WASHING BARS WITH PLATE-LIKE POLYMERIC INCLUSIONS

FIELD OF THE INVENTION

The invention relates to extruded personal washing bar that contains inclusions of plate-like polymer particles to provide unique sensory properties during use. The bar is made by extrusion and has in-use properties which are suitable for the mass market.

BACKGROUND

With the growth of the specialty and artisan soap market, consumers are being offered personal washing bars that provide a wider range of sensory benefits and experiences. There is an ongoing need for technologies that are suitable for personal washing bars targeted to the mass market that provide novel sensory attributes that can be combined in various ways to cue product benefits.

One approach to sensory combinations that is well known in foods is the combination of opposing sensations, e.g., sweet/sour, crunchy/creamy, hot/cold. While exploring such opposing sensations in the context of personal washing, it was discovered that the sensory profile of extruded soap bars that incorporated plate-like inclusions within a certain size range in bar compositions appealed to a segment of consumers. During use, the bars were perceived as having slippery quality overall which consumers like but also had a mildly prickly or scratchy quality. This dual sensation is in contrast to the sensory experience typically provided by exfoliating bars incorporating particles of either smaller size or smaller aspect ratio with which tend to produce a higher friction between the wet bar and skin and are generally perceived as being "draggy" (drag as opposed to slip on the skin).

Consumers who appreciated this combination of tactile attributes associated the sensations with both refreshment and skin care. Surprisingly, the prickly/mildly scratchy sensation produced by these plate-like polymer inclusions in combination with a highly lubricious "background sensation" was perceived to be quite different from the cleansing experience delivered by conventional "exfoliating bars". With the instant bars, the words consumers used to describe the experience were qualitatively different and indicated a more intense association with skin-stimulation, health and wellbeing. Furthermore, when the plate-like inclusions were reflective, the inclusions were perceived as "crystal-like" particles and this visual component intensified the holistic quality of the overall bathing experience.

Common exfoliants used in the art include natural minerals such as silica, talc, calcite, pumice, tricalcium phosphate, and bentonite; seeds such as rice, apricot seeds; crushed shells such as almond and walnut shells; oatmeal and cornmeal; polymer beads such as polyethylene and polypropylene beads; flower petals and leaves; microcrystalline wax beads; and jojoba ester beads.

Various technologies have been disclosed in the art to deliver exfoliation benefits from personal washing bars. These include:

U.S. Pat. No. 6,664,217 to Puvvada et al issued Dec. 16, 2003 discloses toilet bar compositions having simultaneous exfoliating and moisturizing properties delivered via compositions that combine synthetic surfactants, moisturizers and various exfoliating particles.

US 2005/0123574 to Abbas et al published Jun. 9, 2005 discloses a massaging toilet soap containing disintegratable agglomerates. The individual particles comprising the agglomerates include clays (kaolin and bentonite), silica, zeolite, cellulose, various starches and cyclodextrin.

US2003/0219464 to Incando et al published Nov. 27, 2003 discloses methods and means for skin rejuvenation including hair growth stimulation. A derm-brassion compound soap having 0.5% to 99% floured pumice in a glycerin base with 40% honey is disclosed.

US2005/0084470 to Abbas et al published Apr. 21, 2005 discloses skin care and cleansing compositions containing oil seed products particles. The use of native oil seeds; ground, broken or fractured oil seeds; oil seed cakes or blends thereof are disclosed.

WO2006/009625 to Volz et al published Jan. 26, 2006 discloses a soap bar having at least two different potions that differ in solubility by at least 1%. The technology is claimed to deliver a massaging effect.

In contrast, the bars of the present invention incorporate plate-like polymer particles of a specific size range in a continuous phase that provides high lubricity or slipperiness when contacted with water. It is the combination of these specific properties that provides the unusual tactile effects.

SUMMARY OF INVENTION

The personal washing bars of the invention are extruded and preferably stamped bars suitable for mass market applications that incorporate inclusions of plate-like polymer particles into a continuous phase that is predominantly soap. The bars provide a unique combination of sensory attributes. Specifically, the personal washing bar includes:

a. at least about 40% of a soap,
b. from 0.1% to about 20% of a polyol,
c. no more than about 30% water, and
d. from about 0.01% to about 3% based on the weight of the bar composition of inclusions dispersed uniformly in bar, said inclusions comprising plate-like solid polymer particles, having a longest edge dimension in the range from about 50 to about 300 μm, and a thickness such that the ratio of the longest edge dimension to the thickness is in the range from about 1.5:1 to about 15:1, and wherein said personal washing bar is an extruded mass.

In one embodiment, the level of polyol incorporated in the continuous phase of the bar is from about 3% to about 20%, preferably from about 3% to about 15%, and most preferably from about 3% to about 10% based on the total weight of the bar. The incorporation of polyol further increases the lubricity of the bar and lather and is found to complement the opposing prickly sensation produced by the particles.

In another embodiment, the continuous phase of the bar is translucent or transparent. In this embodiment the bar optionally can include a pearlizing agent as it has been found that such materials augment the overall sensory experience provided by the inventive bars.

In another embodiment, the individual plate-like polymer particles are transparent visible mirrors (i.e., have high specular reflectance to light in the visible spectrum). It has been found that polymer particles meeting this reflectivity requirement are perceived by consumers as having an appearance that is reminiscent of small mineral crystals which complements the tactile properties of the particles with a strong visual cue.

In a further and preferred embodiment the bar is a stamped bar characterized by top and bottom stamped faces bounded by a parting line. By the term "stamped bar" is meant a toilet soap bar that is molded into a distinctive shape by stamping or compaction molding with split soap making dies.

These and other embodiments are described more fully below in the following written description.

DETAILED DESCRIPTION OF INVENTION

Figure 1:
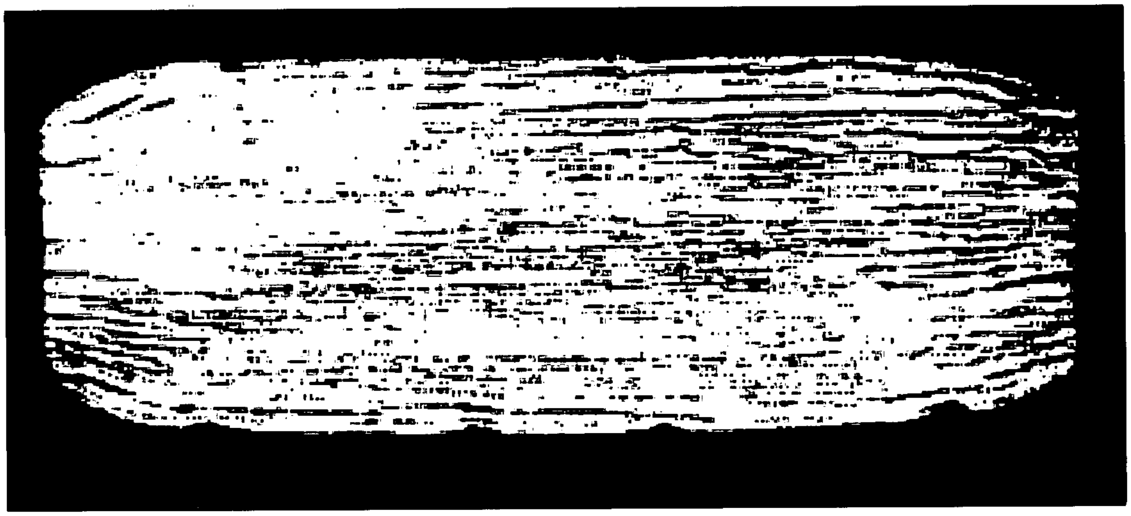
FIG. 1. Photograph of extruded bar shaved along the longitudinal direction, soaked overnight in 3 A alcohol and dried. Note micro-cracks indicated by fine horizontal lines running parallel to the direction of extrusion.

As used herein % or wt % refers to percent by weight of an ingredient as compared to the total weight of the composition or component that is being discussed.

Except in the operating and comparative examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

It should be noted that in specifying any range of concentration, any particular upper concentration can be associated with any particular lower concentration.

For the avoidance of doubt the word "comprising" is intended to mean "including" but not necessarily "consisting of" or "composed of." In other words, the listed steps, options, or alternatives need not be exhaustive.

The present invention relates to extruded personal washing bars that comprise a continuous phase mass into which inclusions of plate-like polymer particles are dispersed. The bars of the invention provide unique visual and tactile properties during use. The term continuous phase is used in its normal sense for dispersions to designate that phase which is continuous throughout the bar and which predominantly controls the physical properties critical to manufacture and dissolution of the bar.

The nature of the continuous phase, the inclusions, various optional ingredients and test methods are described below.

Continuous Phase Mass

The continuous phase comprises surfactants suitable for cleaning the skin which comprise at least about 40%, preferably at least about 55%, more preferably at least about 65% and most preferably at least about 70% of soaps based on the total weight of the bar composition.

The surfactants should be suitable for routine contact with human skin and preferably be high lathering. A variety of surfactants can be employed such as those described in U.S. Pat. No. 6,730,642 to Aronson et al incorporated by reference herein.

The preferred type of surfactant is fatty acid soaps. The term "soap" is used herein in its popular sense, i.e., the alkali metal or alkanol ammonium salts of aliphatic, alkane-, or alkene monocarboxylic acids. Sodium, potassium, magnesium, mono-, di- and tri-ethanol ammonium cations, or combinations thereof, are suitable for purposes of this invention. In general, sodium soaps are used in the compositions of this invention, but from about 1% to about 25% of the soap may be potassium, magnesium or triethanolamine soaps. The soaps useful herein are the well known alkali metal salts of natural or synthetic aliphatic (alkanoic or alkenoic) acids having about 8 to about 22 carbon atoms, preferably about 10 to about 18 carbon atoms. They may be described as alkali metal carboxylates of saturated or unsaturated hydrocarbons having about 8 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It is preferred to use soaps having the fatty acid distribution of coconut oil or tallow, or mixtures thereof, since these are among the more readily available fats. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are C16 and higher. Preferred soap for use in the compositions of this invention has at least about 85% fatty acids having about 12 to 18 carbon atoms.

Coconut oil employed for the soap may be substituted in whole or in part by other "high-lauric" to "lauric rich" oils, that is, oils or fats wherein at least 50% of the total fatty acids are composed of lauric or myristic acids and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter.

A preferred soap is a mixture of about 10% to about 40% derived from coconut oil or other lauric rich oils ("laurics soap") and about 90% to about 60% tallow or other stearic rich oils ("stearics soaps").

The soaps may contain unsaturation in accordance with commercially acceptable standards. Excessive unsaturation is normally avoided because of the potential for rancidity.

Soaps may be made by the classic kettle boiling process or modern continuous soap manufacturing processes wherein natural fats and oils such as tallow, palm oil or coconut oil or their equivalents are saponified with an alkali metal hydroxide using procedures well known to those skilled in the art. Two broad processes are of particular commercial importance. The SAGE process where triglycerides are saponified with a base, e.g., sodium hydroxide and the reaction products extensively treated and the glycerin component extracted and recovered. The second process is the SWING process where the saponification product is directly used with less exhaustive treatment and the glycerin from the triglyceride is not separated but rather included in the finished soap noodles or bars.

Alternatively, the soaps may be made by neutralizing fatty acids, such as lauric (C12), myristic (C14), palmitic (C16), or stearic (C18) acids with an alkali metal hydroxide or carbonate.

A second broad type of surfactant useful in the practice of this invention comprises non-soap synthetic type detergents—so called syndets. Syndets can include anionic surfactants, nonionic surfactants, amphoteric or zwitterionic surfactants and cationic surfactants.

The anionic surfactant may be, for example, an aliphatic sulfonate, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates).

The anionic surfactant can also be a sulfonated fatty acid such as alpha sulfonated tallow fatty acid, a sulfonated fatty acid ester such as alpha sulfonated methyl tallowate or mixtures thereof.

The anionic surfactant may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates or lactylates, $C_8$-$C_{22}$ monoalkyl succinates and maleates, sulphoacetates, and acyl isethionates.

Another class of anionics is $C_8$ to $C_{20}$ alkyl ethoxy (1-20 EO) carboxylates.

Another suitable anionic surfactant is $C_8$-$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms. The acyl isethionate may also be alkoxylated isethionates Acyl isethionates, when present, will generally range from about 0.5 to about 20% by weight of the total composition. Preferably, this component is present from about 1 to about 15% and most preferably from about 1% to about 10% by weight.

In general the anionic component will comprise from about 1 to 20% by weight of the syndet surfactants, preferably 1 to 15%, and most preferably 1 to 5% by weight of the composition.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. Suitable amphoteric surfactants include amphoacetates, alkyl and alkyl amido betaines, and alkyl and alkyl amido sulphobetaines.

Amphoacetates and diamphoacetates are also intended to be covered in possible zwitterionic and/or amphoteric compounds which may be used.

The amphoteric/zwitterionic surfactant, when used, generally comprises 0% to 25%, preferably 0.1 to 20% by weight, more preferably 1% to 10% of the surfactant base.

Suitable nonionic surfactants include the reaction products of compounds having a hydrophobic group and a reactive hydrogen atom, for example aliphatic alcohols or fatty acids, with alkylene oxides, especially ethylene oxide either alone or with propylene oxide. Examples include the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a alkyl polysaccharides and alkyl polysaccharide amides.

Examples of cationic detergents are the quaternary ammonium compounds such as alkyldimethylammonium halogenides.

Other surfactants which may be used are described in U.S. Pat. No. 3,723,325 to Parran Jr. and "Surface Active Agents and Detergents" (Vol. I & II) by Schwartz, Perry & Berch, both of which is also incorporated into the subject application by reference.

In addition to surfactants, the bar can contain various optional ingredients including plasticizing agents, hardening agents, fillers, various adjuvants such as pearlizing agents, and agents that provide skin care benefits. Examples of various materials are described below under OPTIONAL INGREDIENTS.

A second critical component of the continuous phase is a polyol or mixture of polyols. The types of polyols useful in the current invention include relatively short chain polyhydroxy compounds such as propylene glycol, glycerol, sorbitol, manitol; sugars such as sucrose and glucose; carbohydrates such as hydrolyzed starch, dextrin and maltodextrin, and polyalkylene glycols such as polyoxyethylene glycol (PEG) and polyoxypropylene glycol (PPG).

Preferred polyols for use in the current invention are glycerol (glycerin), sorbitol and mixtures of glycerol and sorbitol.

One primary function of the polyol is to provide high lubricity to the bar when it is wetted with water and rubbed on the hands or body. The amount of polyol required to achieve the desired level of lubricity depends to some extent on the surfactant composition and types of additives present in the bar. The minimum levels is about 0.1% based on the weight of the bar. However, the amount of polyol is preferably greater than 1.5%, preferably greater than 2% and more preferably greater than 3% based on the total weight of the bar.

Although the lubricity of the bar increases with its polyol content, there is an upper limit to the amount of polyol that can be incorporated in the continuous phase in the current compositions because of the constraint that the bar must be extrudable. This upper limit is about 20%. Bar compositions having more than about 20% polyol by weight generally become too soft and sticky to extrude and stamp at high speed. Thus, the useful polyol range is about 1% to about 20%, preferably about 1.5% to about 15%, and most preferably about 2% to about 12% by weight based on the total bar composition.

For glycerin, sorbital or their mixtures, a level of polyol between about 3% and about 10% by weight of bar is generally optimal.

It has also been found the water level in the continuous phase is also important to achieve bars that have high lubricity yet are sufficiently hard to be fabricated by extrusion and stamping. The water level also controls the rate at which lubricity develops and too low a water level can lead to excessive hydration times and perceived excessive scratchiness. The optimum water level depends strongly on the level of polyol (e.g., glycerin) present in the continuous phase as well as the process used to make the bar. The water level in the bar can vary after the bar is produced because of evaporation of water and water level thus depends on storage conditions and the effective moisture barrier of the packaging required. Thus, the water level typically ranges from about 3% (or even less in extreme cases) to about 30% by weight of bar depending upon the age of the bar. Preferably, the water level should be greater than about 10% by weight based on the continuous phase.

However, too high a water level generally leads to excessive softening and an inability to extrude and stamp the bar at high speeds. Generally, this occurs when the water level exceeds about 20% by weight of the bar composition, however under some conditions soap bars with as much as 30% water can be effectively extruded.

The maximum level of water that can be used in the continuous phase while still maintaining a sufficiently hard composition for extrusion also depends of the type and level of polyol employed. For liquid polyols such as glycerin, the maximum combined water plus polyol level should generally be less that about 40%, preferably less than 35%, most preferably less than about 25% based on the total weight of the bar. In some cases a combined level less than about 20% is optimal.

In a preferred embodiment of the invention, the continuous phase is transparent or translucent. Tests used to define transparent or translucent compositions based on light transmission are summarized in the TEST METHODOLOGY SECTION. Translucent bars have a light transmission ranging from about 5 to about 40% under the test methods employed. Transparent bars have a transmission greater than 45%.

To achieve bars that are both translucent (or transparent) and extrudable (see below) requires that translucency can not generally be achieved solely by employing very high levels of organic solvents in combination with water to achieve refractive index matching. In general, translucent extruded bars are produced by a combination of intensive mixing and the limited use of water miscible solvents as is described in U.S. Pat. No. 3,864,272 to Toma et al issued Feb. 4, 1975.

Inclusion Phase

The further key component of the invention is the inclusions which comprise distinct plate-like polymer particles that are well dispersed in the continuous phase of the bar. The term plate-like particles is used herein to mean anisotropic particles whose longest edge dimension (e.g. length, diameter or longest axis) greatly exceeds their thickness. For such particles, the ratio of this longest edge dimension (e.g., edge-length, diagonal, diameter, etc.) to the particle thickness is in the range of about 1.5:1 to about 15:1, preferably about 3:1 to about 8.5:1 and most preferably from about 5:1 to about 8:1. Thus, these plate-like polymer particles are not the spherical polymer particles typically used in skin cleaning products to exfoliate.

The faces of the particles can have a variety of shapes including geometric shapes like squares, rectangles, diamonds, rhomboids, hexagons, octagons, circles and oblate spheroids. The particles can also have irregular shapes as well as irregular shapes. Although plates having a smooth edge, e.g., circular or elliptical cylinders, are suitable, plates having straight edges meeting at distinct corners are preferred because of the sensory and optical effects they produce in the bars. Preferred edge shapes are squares, polygons and rectangle.

The longest edge dimension is critical for the performance of the plate-like inclusions in the present invention. The longest edge dimension for squares and rectangular edges is simply the longest edge, while for regular polygons and smooth shaped edges (e.g., circles) the longest edge dimension is taken as the longest diagonal (e.g., diameter in the case of circles).

The longest edge dimension should be in the range from about 50 μm to about 300 μm, preferably from about 50 μm to about 250 μm. Particles with longest dimension less than about 50 μm do not provide sufficient tactile sensation during use while particles having longest edge of greater than about 300 μm are progressively too scratchy and give an unpleasant sensation during use.

It has been found that some consumers prefer the sensory experience provided by smaller particles sizes in the useful range and perceive bars incorporating such particles as more caring to the skin. For this group, the preferred longest edge dimension should be in the range of about 50 μm to about 200 μm, preferably 50 μm to 150 μm, and most preferably 75 μm to about 150 μm.

In contrast, other consumers prefer the more vigorous skin stimulation provided by larger particles within the useful range. For this group, the preferred longest edge dimension should be in the range from about 150 μm to about 300 μm, preferably from about 150 μm to about 250 μm.

The plate-like particles are comprised of a polymeric material. Preferred polymers are thermoplastic polymers (or thermosetting polymers). Suitable thermoplastic polymers include polyesters such as homo- and co- and higher order polymers of polyethylene terephthalate, polybutylene terphthalate, copolymers of terephthalic acid and various glycols such as ethylene glycol or polyalkylene glycols (e.g., PEG and PPG), polyethylene naphthalates and polyoxyethylene naphthalates.

Another suitable class of thermoplastic polymer is acrylic based polymers (designated "acrylates" polymers) and copolymers which include such polymers as polymethyl methacrylate, polymethyl ethyl acrylate and the like.

Another suitable polymer is polystyrene and copolymers of polystyrene with polypropylene and ethylvinyl acrylate.

Especially suitable polymers are polymers selected from the group consisting of polyethylene terephalate, polymethyl methacrylate, polybutlylene terephthalate, glycol modified polyethlene terephthalate, polystyrene, polyethylene naphthalate and combinations thereof.

Particularly suitable are plate-like polymer particle which are laminates comprising polyethylene terephthalate and acrylates copolymers.

It should be understood that the various types of polymers mentioned above can be blends and both chemical blends (co- and higher order, e.g., terpolymers) and physical blend (coextruded or laminated) are useful. Such blends would be within the scope of the present invention.

The polymer comprising the particles should not be too hard in a material sense to avoid excessive scratching of the skin. Preferably, the polymers should have a hardness less than about 3 MOS, more preferably less than 2 MOS.

In addition to their shape and physical dimensions, it is desirable that the plate-like inclusions are sufficiently smooth to act as mirrors to visible light. By the term "mirrors to visible light" or "visible mirrors" is meant that the major surface of the particle is sufficiently smooth to reflects light predominantly by specular reflection as opposed to diffuse reflection. Ideally, the diffuse component of reflection should contribute less than 10%, preferably less than 5% and most preferably less than 1% to the total reflectance of the particle, i.e., the specular reflectance should dominate. The total (specular) reflectance of the particle at the reflection angle should be at least 50%, preferably at least 70% and more preferably greater than 90% of the incident light.

It is also preferably that the plate-like inclusions be comprised of predominantly transparent particles with low overall chromaticity at non-reflecting angles. Preferably their adsorption of visible light should be less than 50%, more preferably less than 30% and most preferably less than 10% of light in the visible spectrum at non-reflecting angles.

It has been found that such transparent, non-absorbing and specularly reflective particles when incorporated in the personal washing bars of the invention are perceived to sparkle without introducing "black spots" which detract from the overall appearance of the bar.

To achieve high specular reflectivity and transparency, the polymer particles should preferably not contain metals such as aluminum, gold or silver, high levels of opacifing or coloring pigments (e.g., TiO2 or colored pigments), or high levels of dyes. Furthermore, the constituent polymer comprising the particle or the layers comprising the particle in the case of laminates should be compatible and not phase separate so as to produce light scattering centers which would make the particles opaque.

Particularly preferred polymers are laminated polymers comprising alternating layers of polyester (e.g., polyethylene or polybutylene terephthalate or naphthalate) and acrylics polymer (e.g., polymethyl methacrylate) that are substantially free of metals, pigments, and opacifiers. Such particles are available from various suppliers including Meadowbrook Inventions Inc (Crystallina); 3M Corporation (Visible Mirror or Colored Mirror Glitters); and Glitterex Corporation (Poly-Flake©).

The level of the plate-like inclusions in the bar is generally in the range from about 0.01% to about 3%. When using particles in the size range of about 150 μm to about 300 μm (e.g., 250 μm) a particle level of about 0.02% to about 0.5% is generally preferred. However, when particles in the smaller size range of are utilized, e.g., 50 μm to about 150 μm, a higher inclusion level can be employed.

Optional Ingredients

Adjuvants

Adjuvants are ingredients that improve the aesthetic qualities of the bar especially the visual, tactile and olefactory properties either directly (perfume) or indirectly (preservatives). A wide variety of optional ingredients can be incorporated in one or more of the phases that comprise the bar composition—generally present in the continuous phase of the bar. Examples of adjuvants include but are not limited to: perfumes; opacifying agents such as higher fatty acids and alcohols, ethoxylated fatty acids, solid esters, and $TiO_2$; dyes and pigments; pearlizing agent; sensates such as menthol and ginger; preservatives such as dimethyloldimethylhydantoin (Glydant XL1000), parabens, sorbic acid and the like; anti-oxidants such as, for example, butylated hydroxytoluene (BHT); fillers that provide creamy lather such as calcium carbonate and talc; chelating agents such as salts of ethylene diamine tetra acetic acid (EDTA) and trisodium etridronate; emulsion stabilizers; auxiliary thickeners; buffering agents; and mixtures thereof.

Particularly useful optional ingredients are pearlizing agents as these materials have been found to complement and actually enhance the overall pleasurable experience of using the bars of the invention and provide bars that are visually very appealing to consumers. A preferred pearlizing agent is $TiO_2$ coated mica (roughly 75% mica/25% $TiO_2$) sold for example by Merck under the trade name Timiron MP 115 and Sudarshan under the trade name Sumica Pearl Silver 43133.

The level of pearlizing agent should be between about 0.1% to about 3%, preferably between 0.1% and 0.5% and most preferably between about 0.2 to about 0.4% based on the total weight of the bar composition.

Skin Benefit Agents

A particular class of optional ingredients highlighted here is skin benefit agents included to promote skin and hair health and condition. Potential benefit agents include but are not limited to: lipids such as cholesterol, ceramides, and pseudoceramides; humectants and hydrophilic skin conditioning agents such as glycerol, sorbitol, propylene glycol, and polyalkalene oxides polymers and resins; antimicrobial agents such as TRICLOSAN; sunscreens such as cinnamates; other types of exfoliant particles such as polyethylene beads, walnut shells, apricot seeds, flower petals and seeds, and inorganics such as silica, and pumice; additional emollients (skin softening agents) such as long chain alcohols and waxes like lanolin; additional moisturizers; skin-toning agents; skin nutrients such as vitamins like Vitamin C, D and E and essential oils like bergamot, citrus unshiu, calamus, and the like; water soluble or insoluble extracts of avocado, grape, grape seed, myrrh, cucumber, watercress, *calendula*, elder flower, geranium, linden blossom, amaranth, seaweed, gingko, ginseng, carrot; *impatiens balsamina*, camu camu, alpina leaf and other plant extracts such as witch-hazel, and mixtures thereof.

The composition can also include a variety of other active ingredients that provide additional skin (including scalp) benefits. Examples include anti-acne agents such as salicylic and resorcinol; sulfur-containing D and L amino acids and their derivatives and salts, particularly their N-acetyl derivatives; anti-wrinkle, anti-skin atrophy and skin-repair actives such as vitamins (e.g., A, E and K), vitamin alkyl esters, minerals, magnesium, calcium, copper, zinc and other metallic components; retinoic acid and esters and derivatives such as retinal and retinol, vitamin B3 compounds, alpha hydroxy acids, beta hydroxy acids, e.g. salicylic acid and derivatives thereof; skin soothing agents such as aloe vera, jojoba oil, propionic and acetic acid derivatives, fenamic acid derivatives; artificial tanning agents such as dihydroxyacetone; tyrosine; tyrosine esters such as ethyl tyrosinate and glucose tyrosinate; skin lightening agents such as aloe extract and niacinamide, alpha-glyceryl-L-ascorbic acid, aminotyroxine, ammonium lactate, glycolic acid, hydroquinone, 4 hydroxyanisole, sebum stimulation agents such as bryonolic acid, dehydroepiandrosterone (DHEA) and orizano; sebum inhibitors such as aluminum hydroxy chloride, corticosteroids, dehydroacetic acid and its salts, dichlorophenyl imidazoldioxolan (available from Elubiol); anti-oxidant effects, protease inhibition; skin tightening agents such as terpolymers of vinylpyrrolidone, (meth) acrylic acid and a hydrophobic monomer comprised of long chain alkyl (meth)acrylates; anti-itch agents such as hydrocortisone, methdilizine and trimeprazine hair growth inhibition; 5-alpha reductase inhibitors; agents that enhance desquamation; anti-glycation agents; anti-dandruff agents such as zinc pyridinethione; hair growth promoters such as finasteride, minoxidil, vitamin D analogues and retinoic acid and mixtures thereof.

Extruded Mass

The personal washing bars described herein are extruded masses. By the term "extruded masses" is meant that the bars are made by a process which involves both the intensive mixing or working of the soap mass while it is in a semi-solid plastic state and its forming into a cohesive mass by the process of extrusion.

The intensive mixing can be accomplished by one or more unit operations known in the art which can include roller milling, refining, and single or multistage extrusion. Such processes work the bar mass, e.g., soap mass, at a temperature between about 30° C. and about 50° C. to form a homogeneous network of crystals of insoluble surfactant dispersed in a viscous liquid crystalline phase containing the lower melting, more soluble surfactants (e.g., soaps).

An extruded mass must be thermoplastic within the process temperature of extrusion which is generally between about 30° C. and about 45° C., preferably at a temperature between about 33° C. to about 42° C. Thus, the material must soften within this process temperature window but remain highly viscous, i.e., not softer excessively to form a sticky mass. The material must regain its structure and harden quickly as the temperature is lowered below its softening point. This means that the internal structure must reform quickly generally by re-solidification of structure forming units, e.g., crystals.

Furthermore, the softened mass although pliable must be sufficiently viscous so that is does not stick to the surfaces of the extruder in order to be capable of conveyance by the extruder screws but not bend excessively when exiting the extruder as a billet. However, if the mass is too viscous it will not be capable of extrusion at reasonable rates. Thus, the hardness of the mass should fall within limits within the process temperature window to be capable of high rates of production. By high rate of production is meant in excess of about 50 tablet or bars per minute (4.5 Kg/min for a 90 Kg bar), preferably greater than about 150 bars per minute (13.5 Kg/min), more preferably greater than 250 bars per minute (22.5 Kg/min) and still more preferably greater that 400 bars per minute (36 Kg/min).

Personal washing bars formed by extrusion (also commonly known as milled soaps) have physico-chemical properties and an internal structure which are quite different from soaps that are made by a melt-cast process wherein the bar composition is first melted at high temperature (e.g., 70° C.) to form a liquid phase which is then poured into molds to solidify by quiescent cooling.

These differences in internal structure, composition and physico-chemical characteristics provide extruded personal washing bars with overall in-use properties which are better suited for the mass market than cast soaps. These properties include: much lower wear rates, more resistance to scuffing and denting, and a richer, more creamy opaque lather.

The one or more key properties that serve as characteristic "finger-prints" of an extruded mass are structural anisotropy, the level of high melting point materials such as stearic soaps, high melting point and thermal reversibility, and rapid recovery of hardness after heating and shear. These characteristics are briefly described below.

Structural Anisotropy

Bars made by extrusion typically have a characteristic anisotropic internal structure both with respect to the alignment of crystals and overall macro-structure.

One important element of the macro-structure is the "candle structure", disclosed for example by Schonig et al in U.S. Pat. No. 4,720,365 which is produced in the plodder and modified in the stamper. Shear forces generated at the eye-plate and subsequent extensional forces in the plodder cone produce marked alignment within the candles and thus influence the colloidal structure of the extruded mass. Although there is some modification of alignment after stamping, the resultant bar usually has a characteristic macroscopic alignment of the crystallites and domains relative to the bar surface and some residual candle structure.

The liquid (crystalline) phase generated at the extrusion temperature has a relatively lower viscosity and is expected to preferentially flow to the surface of the candles during the plodder compression stage.

In contrast, melt-cast bars have a predominantly isotropic structure because crystallization occurs during quiescent cooling and thus the alignment of crystals is minimal and there is no candle structure.

The differences in internal structure between extruded and melt-cast bars can be visualized by a simple ethanol extraction procedure. In this procedure bars are shaven, for example with a plane of mandolin to reveal inside surfaces (the bars can be shaved in several orthogonal directions). These shaved sections are then immersed overnight in anhydrous 3-A alcohol. After removal from the alcohol, the bars are allowed to dry by standing. A pattern of small cracks appears such as is shown in FIG. 1. These cracks are indicative of the orientated micro-structure of the bar. The alcohol extracts the more soluble soaps in extruded bars, thus exposing the candle structure interface and the lines of flow. In melt-cast bars flow lines and the candle structure are absent and fine cracks are much less pronounced or absent after alcohol emersion.

In addition to the alignment of soap crystals caused by extrusion the extrusion shear field also tends to align the plate-like inclusions employed in the current bars in the direction of extrusion (plates align parallel with the top and bottom surface of the bar). Surprisingly, this phenomenon can improve the overall sensory experience provided by the inclusions during use by for example moderating their tendency to scratch the skin.

Level of High Melting Materials

In order to achieve the rheological properties required for milling and extrusion, an extruded mass must have a sufficient level of solid particles to adequately structure the mass at the process temperature, i.e., the bar contains materials whose melting point is above the extrusion temperature.

For bars that are comprised predominantly of soap, these high melting solids are provided in at least part by the stearic soaps which include the C16 and C18 saturated soaps.

The level of high melting solids (melting point greater than the extrusion temperature) found in extruded bars is generally greater than 15%, typically greater than 25%. For an extruded mass predominantly comprised of soap the level of stearic soaps is generally between about 15% and about 45% based on the total weight of bar, preferably between 25% to about 40%. Other sources of solid particles, e.g., inorganic fillers, can of course also be present.

Melting Point and Thermal Reversibility

Because of the presence of significant high melting solids (e.g. steric soaps and optional fillers) and the lower levels of liquids relative to cast soaps, extruded masses have melting points that are generally above 80° C., typically above 90° C. and usually above 100° C. In contrast, cast soaps generally melt at temperature between 70° C. and 80° C.

Furthermore an extruded mass regains its structure and harden quickly as the temperature is lowered below its softening point. This means that the internal structure reform quickly, generally by re-solidification of structure forming units, e.g., soap crystals. This rapid re-solidification is generally observed as thermal reversibility in differential scanning calorimetry (DSC). By the term thermal reversibility is meant that increasing and decreasing temperature sweeps tend to be super impossible albeit offset by a temperature difference characteristic of the composition. In contrast, cast soaps require much longer periods of time to reform the solid structural units and exhibit lower thermal reversibility, e.g., increasing-decreasing temperature sweeps are either not super-imposable or are offset by much larger temperatures than is found with an mass.

Recovery of Hardness after Heating and Shear

An extruded mass must soften when it is heated to the extrusion process temperature which is typically in the range of about 35° C. to about 45° C. However, at this temperature it must retain sufficient hardness. It has been found experimentally that to achieve the desired rates of production, the hardness of the mass should generally be at least about 1500 g, but generally not greater than about 8000 g, preferably greater than about 4500 g, and more preferably at least about 5000 g as measured by the Hardness Penetration Test described in the TEST METHODOLOGY section, said measurement being carried out at a temperature in the range of about 35° C. to about 45° C.

An extruded mass also remains cohesive after its has been subjected to sheer at the extrusion temperature without exhibiting excessive pliability or stickiness. By the term "remain cohesive" is meant when compacted under pressure the mass should be capable of sintering together to form a single cohesive unit that has mechanical integrity.

Finally, it has been found that an extruded mass quickly recovers its yield stress (as measured by its penetrometer hardness) when it is subjected to shear at the extrusion temperature (e.g., 40° C.) and allowed to cool. For example when the extrudate is cooled after extrusion to 25° C., the mass should recover at least about 75%, preferably at least about 85% and more preferably at least about 95% of the initial hardness before it was sheared, by for example, extrusion through an "orifice" extruder—see below.

The influence of shear on cohesivity, stickiness, pliability and recovery of yield stress can be assessed utilizing an "orifice" extruder which provides a controlled extensional flow similar to that encountered by the mass during extrusion through an eye plate. This device comprises a thermal jacketed barrel (e.g. 350 mm length by 90 mm in diameter) ending in a narrow opening (typically 2-4 mm) and a plunger which is coupled to a drive unit e.g., Instron Mechanical Tester. The plunger forces the mass through the orifice to form an extrudate. The extrudate can be assessed at the process temperature.

The extrudate can be placed in the barrel of the oriface extruder, compressed under different loads and removed to determine its cohesivity or extent of cohesion, its stickiness and its ability to recover its hardness after it has been sheared at the extrusion temperature (e.g., 40° C.) and cooled (e.g., 25° C.).

Based on the above extrudability criteria, so called melt and pour compositions such as those used to make glycerin soaps that require casting in molds in order to form bars are not extrudable masses when they are initially formed from the melt and are not suitable as the continuous phase. Thus, after a cast melt composition is melted and allowed to solidify in a mold for several hours, the composition does not does not form a cohesive non-sticky mass after extrusion through an orifice extruder and the extrudate does not exhibit the required recovery of hardness after cooling.

In addition to the requirement of being suitable for extrusion, the bar mass should also be sufficiently hard to be stamped with conventional soap making dies. The stamping process involves placing a billet or ingot of the extruded mass into a split mold comprised of generally two moveable halves (the dies). These dies when closed compress the billet ("stamp" the billet), squeezing out excess mass and defining the ultimate shape of the bar. The mold halves meet at a parting line which becomes visible as a line on the edge perimeter of the molded finished bar (stamped bar). Thus, a stamped personal washing bar can be characterized as comprising top and bottom stamped faces meeting at a parting line.

Experience has shown that stamping can be achieved by ensuring that an extruded billet of the bar mass (also known as an ingot) has a minimum hardness of at least about 1500 g at the stamping temperature which is typically in the range 25° to 45° C.

The one or more key characteristics of an extruded mass are summarized in the table below.

| CHARACTERISTIC PROPERTY | EXTRUDED MASS | CAST SOAP |
|---|---|---|
| Structural anisotropy | Aligned crystals<br>Distinct flow lines/candle structure evident as small cracks formed after alcohol emersion | generally random crystal orientation<br>Absence of candle structure<br>No prominent and systematic lines or cracks evident after alcohol emersion |
| Levels of stearic soaps ($C_{16}/C_{18}$ soaps) | 15% to about 45% based on the total weight of bar, preferably between 25% to about 40%. | Generally less than 15% |
| Melting point/Thermal characteristics | Melting point above 80° C., typically above 90° C. and usually above 100° C..<br>Relatively high degree of thermal reversibility (DSC) | Melting point 70° C. and 80° C..<br>Relatively low degree of thermal reversibility |
| Recovery of hardness after heating and shear | Recovers at least about 75%, preferably at least about 85% and more preferably at least about 95% of its initial hardness before shearing.<br>Forms cohesive mass after extensional shear (Orifice extruder) | After melting and casting ether low recovery of hardness after shear and/or lack of formation of cohesive mass after shear (excessive fracture or softening) |

Test Methodology

Bar Hardness—Penetrometer Hardness Test

A variety of methods are known in the art to measure the hardness of soft solids such as toilet soaps. The techniques used in the current work, is the Penetration Test which measures the penetration of a needle or tapered rod under load. The distance traveled (penetration of the needle into the test mass) under a constant load or the load required to produce a given distance of penetration can be measured. In the test method used in the present work, the latter measurement approach is employed, i.e., variable load to achieve fixed penetration depth.

Although the invention is described by parameters that are measured by the Penetration Test, various hardness tests can be used and inter-correlated with the methods used herein.

Hardness penetration measurements were made using finished toilet soap bars using the TA-XT Plus Texture Analyzer supplier by Stable Micro Systems.

The rheological parameters of the finished bars were determined by measuring the weight necessary for the test probe to penetrate the sample to a distance of 15 mm (see table below). The 30° conical test probe is made from X2 stainless steel and the dimensions are: Length, 60.4 mm; Diameter 30 mm.

The TA-XT Plus Texture Analyser allows for various preset probe speeds. In the examples described herein, the measurements were carried out at a probe speeds of 1 mm/sec. Shear stresses and shear rates were calculated and charts were built. The rheological parameters were finally calculated by least-squares utilizing the Herschel-Bulkley equation:

$$\sigma=\sigma_0+\kappa\gamma^n$$

where $\sigma$ is the shear stress, $\sigma_0$ is the yield stress, k stands for the consistency index, n is the flow index and $\gamma$ is the shear rate.

The instrument parameters used in hardness analyses with TA-XT Express are given in the table below

| Parameters | Value |
|---|---|
| Load cell capacity (kg) | 10 |
| Pre-speed (mm/s) | 2 |
| Return speed (mm/s) | 10 |
| Conical Probe Angle (°) | 30 |
| Trigger Force (g) | 5 |
| Test speed (mm/s) | 1 |
| Distance of penetration (mm) | 15 |

Stickiness was measured using the TA-XT Plus Texture Meter using the compression mode and by acquiring the peak reading when a 45° conical probe left the sample. The other parameters were: penetration distance 10 mm, pre-test speed (10 $mm \cdot s^{-1}$), test speed (1 $mm \cdot s^{-1}$), and post-test speed (10 $mm \cdot s^{-1}$).

Soap Transparency/Translucency Test

The degree of transparency was measured using a light transmission tester model EVT 150 manufactured by DMS—Instrumentacao Cientifica Ltd. The instrument consists of a light source providing a 1.5 cm circular beam, a detector fitted to an analog meter, and a sample holder. The measurement procedure is as follows.

The instrument is first set to 100% transmission in air (i.e., without a test sample). The test sample of the bar material, approximately 90 g, having a thickness of 3 cm is placed in the sample chamber and the % transmission relative to air is measured.

Normal opaque soap bars have 0% transmission, while translucent bars have a transmission ranging from about 5 to about 40%. Highly transparent bars such as those made by melt-cast processes have a transmission generally greater than 45%.

It has been found that discontinuous phase compositions having a % transmission difference relative to the continuous phase of greater than about 5% are perceived as visually distinctive. Preferably, the difference in light transmission between the phases should be greater than 10%.

Wear Rate Test

The intrinsic wear rate of the mass e.g., individual phases or finished bar is measured by the following procedure.

Four weighed samples of each test bar are placed on soap trays. Two types of soap trays are employed: those that have drainers or raised grids so the water left on the bar after rinsing is drained away; and no drainers so that water can be added to the tray to allow the bars to become "water-logged". The trays are coded as follows:

| With drainers? | Wash temperature (° C.) |
|---|---|
| Yes | 25 |
| Yes | 40 |
| No | 25 |
| No | 40 |

10 ml of distilled water (ambient temperature) are poured into the undrained tray (25° and 40° C.).

Each tablet of soap as follows:

Fill washing bowl with about 5 liters of water, at the desired temperature (20° C. or 40° C.).

Mark the tablet to identify top face (e.g. make small hole with a needle).

Wearing waterproof gloves, immerse the tablet in the water, and twist 15 times (180° each time) in the hands above water.

Repeat the above step

Briefly immerse tablet in the water to remove lather.

Place tablet back on its soap tray, ensuring that the opposite face is uppermost (i.e. the unmarked face).

The above procedure is carried out 6 times per day for 4 consecutive days, at evenly spaced intervals during each day. Alternate face of each bar is placed in the down downward position (facing the bottom of the tray) after each washdown. Between washdowns the soap trays should be left on an open bench or draining board, in ambient conditions. After each washdown cycle, the position of each soap tray/tablet is changed to minimize variability in drying conditions.

At the end of each day each soap tray with drainer is rinsed and dried. Soap trays without drainers are refilled with 10 ml distilled water (ambient temperature). After the last washdown ($4^{th}$ day), all soap trays are rinsed and dried. Each washed bar is placed in its tray and allowed to dry for up to a period of 9 days. On the $5^{th}$ day afternoon, the samples are turned so that both sides of the tablet dry. On the $8^{th}$ day, each tablet is weighed.

The rate of wear is defined as the percent weight loss as follows:

$$\%\ \text{Wear} = \frac{(\text{initial weight} - \text{final weight}) * 100}{\text{initial weight}}$$

EXAMPLES

The following non-limiting examples illustrate various aspects of the invention and preferred embodiments.

Example 1-5

The bar compositions shown in Table 1 were prepared using conventional equipment used in the manufacture of extruded translucent soap. In summary, the composition was prepared by combining soap noodles (e.g., sodium soaps formed by the saponification of a mixture of 85% Tallow and 15% palm kernel oil triglycerides with caustic soda) with the remaining ingredients in Table 1 in a Z-blade mixer and passing the mixture through a 3-roll mill and a refiner. (Note that water addition may not be required if sufficient water is present in the soap noodles). The composition so processed was added to the hopper of a two stage extruder and extruded at a temperature of 35° C. at an extrusion rate of 1.2-4.0 kg/min through an eyeplate having a 3.5×3.5 cm cross section to form billets cut to about 12 cm in lengths. The billets were then transferred to a manual soap stamper and stamped to form the finished personal washing bar utilizing a die set defining a mold having a volume of approximately 89 $cm^3$ (bar with 90 g).

The continuous phases of the bars of Examples 1, 2, 4, 5 are translucent masses (% transmission between 5 and 45%) while the continuous phase of Example 3 is opaque.

The finished bars were attractive in appearance and provided unique tactile properties during use. When wet with water, the bars were perceived as being lubricious and slightly "scratchy" or "prickly". Ex 1-2 and Ex 4-5 bars which contained higher levels of polyol were perceived as even more slippery in use. This dual skin sensation was liked by a segment of consumers who perceived the bar provided a refreshing and beneficial experience. These consumers readily associated the inclusions which appeared as small crystals to provide benefits in polishing, exfoliating and stimulating the skin.

TABLE 2

Compositions of comparative examples C1-C4

| INGREDIENTS | C1 | C2 | C3 | C4 |
|---|---|---|---|---|
| | Wt % | | | |
| ASA D Palmitic/Stearic | 13.70 | 13.70 | 13.70 | 13.70 |
| Lauric Fatty Acid | 3.35 | 3.35 | 3.35 | 3.3e5 |
| Coconut Fatty Acid C12-C18 | 12.60 | 12.60 | 12.60 | 12.60 |
| Hydroxy Stearic Acid HSA | 2.90 | 2.90 | 2.90 | 2.90 |
| Caustic Soda (100%) | 5.36 | 5.36 | 5.36 | 5.36 |
| SMBS (Sodium Metabisulfite) | 0.60 | 0.60 | 0.60 | 0.60 |
| Sorbitol A (100%) | 8.75 | — | — | — |
| Sorbitol B (100%) | 8.75 | — | — | — |
| Glycerin (100%) | — | 17.50 | 8.75 | 4.37 |
| Sucrose Syrup (100%) | — | — | 8.75 | 13.12 |
| Polyethylene Glycol | 80 | 8.0 | 8.0 | 8.0 |
| IPA | — | 2.5 | 2.5 | 2.5 |
| EDTA | 0.2 | 0.2 | 0.2 | 0.2 |
| EHDP | 0.1 | 0.1 | 0.1 | 0.1 |
| SLS | 7.0 | 7.0 | 7.0 | 7.0 |
| Perfume | 1.7 | 1.7 | 1.7 | 1.7 |

TABLE 1

Compositions of Examples 1-5

| INGREDIENTS | EX 1 | Ex 2 | Ex 3 | Ex 4 | Ex 5 |
|---|---|---|---|---|---|
| | Wt % based on total bar composition | | | | |
| CONTINUOUS PHASE | | | | | |
| Sodium soaps from 85/15 Tallow/palm kernel oil | 76.32 | | | | |
| Distilled fatty acid soap 80/20 | | 78.72 | | | |
| Sodium soaps from 80/20 tallow/coconut oil | | | 81.9 | | |
| Sodium soaps from 65/35 coconut oil/palm kernel oil Please check | | | | 78.52 | |
| Sodium soaps from 70/30 palm oil-palm stearin/palm kernel oil | | | | | 84.82 |
| Glycerin | 4 | 3.3 | 0.2 | 3.3 | 8.4 From the Noodle |
| Coconut Fatty Acids | 0.5 | | | | |
| Lauric Fatty Acid | | | | | 2 |
| Minors (color, fragrance, preservatives) | 1.35 | 1.15 | 1.35 | 1.35 | 1.35 |
| Water | 17.5 | 16.5 | 16.5 | 16.5 | 11.5 |
| Translucency (% Transmission) of continuous phase | 10-20 | 10-20 | ~0 | 10-20 | 10-20 |
| Penetrometer Hardness (g) range 33° C. to 45° C. | 5000.0 | 5500.0 | 6000.0 | 5500.0 | 5000.0 |
| INCLUSIONS | | | | | |
| Polyethylene terephthalate/acrylates copolymer (Crystalina 321) Average longest edge dimension 200 µm Average thickness 34 µm | 0.08 | 0.08 | 0.08 | 0.08 | 0.08 |
| PEARLIZING AGENT | | | | | |
| Titanium coated mica | 0.25 | | | 0.25 | 0.25 |

Comparative Examples C1-C4

The compositions of comparative examples C1-C4 are given in Table 2. All of these compositions can be formed into bars by a melt-cast (or melt & pour) process. However, none of the compositions can be formed into bars by extrusion. When heated to a extrusion temperature and sheared, each mass became excessively soft and sticky.

TABLE 2-continued

Compositions of comparative examples C1-C4

| INGREDIENTS | C1 | C2 | C3 | C4 |
|---|---|---|---|---|
| | Wt % | | | |
| Post Dosed Water | 31.23 | 36.14 | 43.03 | 25.76 |
| Transparency (% Transmission) of continuous phase | 44.7 | 49.7 | 60.2 | 58.9 |

TABLE 2-continued

| Compositions of comparative examples C1-C4 | | | | |
|---|---|---|---|---|
| INGREDIENTS | C1 | C2 | C3 | C4 |
| | Wt % | | | |
| INCLUSIONS | | | | |
| Polyethylene terephthalate/acrylates copolymer (Crystalina 321) | 0.08 | 0.08 | 0.08 | 0.08 |
| PEARLIZING AGENT | | | | |
| Titanium coated mica | 0.25 | 0.25 | 0.25 | 0.25 |

Example 6-9 and Comparatives 5-9

These example and comparatives illustrates the influence of the particles size and concentration of the inclusions on the in-use properties of the cleaning bars.

Various Bars were prepared using the same composition as was used in Ex 1 (see Table 1). These bars only differed with respect to the dimensions (largest particle dimension) of the plate-like polymer inclusions and the amounts used in the bars. The bars were prepared according to the methods described in Examples 1-5.

The dimensions of the particles and a summary of relevant sensory observations of the exemplary bars (Ex 6-Ex 9) and comparative bars (C5-C9) are given in Table 3.

Several points are noteworthy.

Bars that contain inclusions falling within the range of length dimensions between about 150 and 300 microns present at a concentration between 0.015 and 0.1 wt % (Ex 6 and Ex 7) appear pearlescent with small reflecting flickers of light. These bars have a characteristic feel in use of being both highly lubricious and mildly scratchy which a group of consumers perceive as highly stimulating and find this combination of sensory properties beneficial.

In contrast, bars having too high a proportion of particles (C5) loose most of their lubricity and feel abrasive and excessively scratchy even when the particles have the correct edge length. The optimum concentration of plate-like polymer particles depends upon the composition of the bar, especially the level and type of polyol and additives used. The optimum concentration of particles in the size range of 150 to 300 μm is generally less than 1%, preferably less than 0.2%.

Bars that have plate-like inclusions that are larger than the maximum edge length of about 300 μm (C6-C9) are perceived as very scratchy in use and can in fact damage the skin. These bars are not liked by consumers and have a further negative in potentially leaving a noticeable residue of the large particles on surfaces such as the walls and floors of the shower.

Inclusions having a largest edge length of between 50 μm and 150 um e.g., 100 μm (Ex 8) and 50 μm (Ex 9) yield bars which are perceived as being lubricious and only slightly prickly or scratchy. Bars incorporating these smaller particles are more appealing to other groups of consumers who perceive these bars to be more gentle to the skin and provide a "polishing effect".

Thus, by controlling the largest dimension of the plate like particles bars supporting different sensory propositions that appeal to different consumer groups can be prepared.

Inclusions having an edge lengths less than about 50 μm have negligible sensory impact (C9).

TABLE 3

| Description of Exemplary bars Ex 10-12 and Comparative C5-C9[a)] | Ex 6 | C5 | Ex 7 | Ex 8 | Ex 9 | C6 | C7 | C8 | C9 |
|---|---|---|---|---|---|---|---|---|---|
| Average longest edge dimension (μm) | 250 | 200 | 175 | 100 | 50 | 650 | 1000 | 3000 | 35 |
| Concentration of inclusions (%) | 0.1 | 3.2 | 0.5% | 0.2 | 0.2 | 0.08 | 0.08 | 0.08 | 0.08 |
| Sensory Properties | | | | | | | | | |
| Appearance | Pearlized small reflective specs | Pearlized Numerous small reflective specs | Pearlized small reflective specs | Pearlized small reflective specs | Pearlized particles less pronounced | Pearlized reflective specs | Pearlized Larger reflective specs | Pearlized Large reflective specs | Pearlized lustrous particles difficult to detect |
| Feel in use | Slippery + scratchy | Some slip too scratchy | Slippery + slightly scratchy | slippery less scratchy | slippery marginally scratchy | Little or no slip, very scratchy | No slip very scratchy | No slip very scratchy | slippery |
| Residue[b)] | negligible residue | Some residue | negligible residue | No Residue | No Residue | some residue | some residue | some residue | No Residue |

Notes:
[a)]The continuous phase of all bars is the composition used in Ex 1 and identified in Table 1. All bars contained 0.25% titanium coated mica.
[b)]The term "Residue" refers to the presence to inclusion particles left on the surfaces of the shower cabinet or sink after use of the bar, i.e., after washing and rinsing.

Example 10 and 11

The bar composition shown in Table 4 were prepared by the methods set forth in Example 1-5.

Ex 10 is the same composition as Ex 1 but without the coated mica pearlizing agent. This bar is translucent and provides the dual slippery/prickly sensation characteristic of the bars of the invention.

Ex 11 has the same continuous phase composition as Ex 9 but 10% of the continuous phase is replaced with sodium carbonate. The bar is opaque. Although this bar produces a creamy lather, and provides a pleasant in use sensation, it is perceived as creamy but the bar is markedly less lubricious and slippery in the hands and the sensation of scratchiness is more pronounced. Overall, this bar is less preferred than bars of Ex 9 by consumers who appreciate the dual tactile sensation.

It has been generally been found that consumers prefer embodiments of the present invention in which the continuous phase is either translucent or transparent compared with variants in which the continuous phase is opaque.

TABLE 4

Compositions of Examples 10 and 11

| INGREDIENTS | Ex 10 (Wt % based on total bar composition) | Ex 11 (Wt % based on total bar composition) |
|---|---|---|
| CONTINUOUS PHASE | | |
| Sodium soaps from 85/15 Tallow/palm kernel oil | 76 | 69% |
| Glycerin | 4 | 3.6 |
| Coconut Fatty Acids | 0.5 | 0.45 |
| Minors (color, fragrance, preservatives) | 1.35 | 1.2 |
| Calcium Carbonate | | 10 |
| Water | 17.5 | 15.75 |
| Translucency (% Transmission) of continuous phase | 10-20 | <5 |
| INCLUSIONS | | |
| Polyethylene terephthalate/acrylates copolymer (Crystalina 321) Average longest edge dimension 200 μm Average thickness 34 μm | 0.08 | 0.08 |

Example 12

Especially preferred personal washing bars are extruded bar consisting of the ingredients listed in Table 5 with the obvious constraint that the sum of the ingredients can not exceed 100% so that all or some of the individual ingredients can not be simultaneously present at their maximum levels.

TABLE 5

Highly preferred bar compositions

| Ingredient | Range (wt %) about | Preferred types |
|---|---|---|
| Soaps | 50-80 | Na, K, TEA soaps 90/10 to 60/40 Strearics/Laurics |
| Polyols | 0.1-12 | glycerol, sorbitol, and/or propylene glycol |
| Water | <30% | preferably less than 20%, more preferably between about 3% and 15% |
| Plate-like polymer particles | 0.1-3 | 150-250 μm and or 50-150 μm polyethylene terephalate, polymethyl methacrylate, polybutlylene terephthalate, glycol modified polyethlene terephthalate, polystyrene, polyethylene naphthalate and combinations thereof |
| Fatty acids | 0-5 | $C_{12}$-$C_{18}$ fatty acids |
| Syndets | 0-5 | alkyl and alkylethoxy sulfates, acyl isethionates |
| Electrolytes | 0-2 | NaCl, KCl, sodium citrate |
| Pearlizing agent | 0-3 | Titanium coated mica |
| Adjuvants | 0-5 | As described above, especially: perfumes, colorants, preservatives, opacifiers, and fillers |
| Skin benefit agents | 0-5 | As described above, especially: antimicrobials, vitamins, essential oils, plant extracts, emollients, and moisturizers |

The invention claimed is:

1. An extruded personal washing bar providing unique combination of sensory attributes, said bar comprising:

a. at least about 40% of a soap, b. from 0.1% to about 20% of a polyol, c. no more than about 30% water, and d. from about 0.01% to about 3% based on the weight of the bar composition of inclusions dispersed uniformly in bar, said inclusions comprising plate-like solid polymer particles having a longest edge dimension in the range from about 50 to about 300 μm, and a thickness such that the ratio of the longest edge dimension to the thickness is in the range from about 1.5:1 to about 15:1, and wherein said personal washing bar is an extruded mass and each plate-like solid polymer particle is a laminate comprising a mixture of polyethylene terephthalate and acrylates copolymers.

2. A personal washing bar according to claim 1 comprising at least 55% soap.

3. A personal washing bar according to claim 1 comprising at least 70% soap.

4. A personal washing bar according to claim 1 further comprising a syndet surfactant.

5. A personal washing bar according to claim 1 comprising from about 3% to about 20% water.

6. A personal washing bar according to claim 1 wherein the polyol comprises about 3% to about 10% by weight of the bar.

7. A personal washing bar according to claim 1 wherein polyol is glycerin, sorbitol or a mixture of glycerin and sorbitol.

8. A personal washing bar according to claim 1 wherein the bar is translucent or transparent.

9. A personal washing bar according to claim 1 wherein the plate-like polymer particles are present in the amount from about 0.02% to about 0.5% based on the total weight of the bar composition.

10. A personal washing bar according to claim 1 wherein the plate-like polymer particles comprising the inclusions have a longest edge dimension in the range from about 150 μm to about 250 μm.

11. A personal washing bar according to claim 1 wherein the plate-like polymer particles comprising the inclusions have a longest edge dimension in the range from about 50 μm to about 150 μm.

12. A personal washing bar according to claim 1 wherein the plate-like polymer particles comprising the inclusions are visible mirrors.

13. A personal washing bar according to claim 1 wherein the plate-like polymer particles comprising the inclusions are transparent.

14. A personal washing bar according to claim 1 wherein the plate-like polymer particles comprising the inclusions have an adsorption of light in the visible spectrum of less than 10% of the incident light at non-reflecting angles.

15. A personal washing bar according to claim 1 wherein each plate-like polymer particle has a specular reflectivity of at least about 50%.

16. A personal washing bar according to claim 1 further comprising a pearlizing agent.

17. A personal washing bar according to claim 1 wherein the pearlizing agent is a titanium coated mica.

18. A personal washing bar according to claim 1 wherein the bar is comprised of a single continuous phase.

19. A personal washing bar according to claim 1 wherein the personal washing bar is a stamped bar characterized by top and bottom stamped faces meeting at a parting line.

* * * * *